(12) United States Patent
Coates

(10) Patent No.: US 10,861,157 B2
(45) Date of Patent: Dec. 8, 2020

(54) SYSTEM AND METHODS FOR DETERMINING MODIFIED FRACTIONAL FLOW RESERVE VALUES

(71) Applicant: MEDTRONIC VASCULAR, INC., Santa Rosa, CA (US)

(72) Inventor: Paul Coates, Corte Madera, CA (US)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 52 days.

(21) Appl. No.: 16/375,076

(22) Filed: Apr. 4, 2019

(65) Prior Publication Data

US 2020/0320706 A1  Oct. 8, 2020

(51) Int. Cl.
*G06T 7/00* (2017.01)
*A61B 6/00* (2006.01)
*A61B 5/0215* (2006.01)

(52) U.S. Cl.
CPC .......... *G06T 7/0014* (2013.01); *A61B 5/0215* (2013.01); *A61B 6/481* (2013.01); *A61B 6/485* (2013.01); *A61B 6/504* (2013.01); *A61B 6/5217* (2013.01); *G06T 2207/20101* (2013.01); *G06T 2207/30096* (2013.01); *G06T 2207/30104* (2013.01)

(58) Field of Classification Search
CPC ......... G06T 7/0014; G06T 2207/20101; G06T 2207/30096; G06T 2207/30104; A61B 5/0215; A61B 6/481; A61B 6/485; A61B 6/504; A61B 6/5217
See application file for complete search history.

(56) References Cited

U.S. PATENT DOCUMENTS

| | | | |
|---|---|---|---|
| 7,155,046 B2 | 12/2006 | Aben et al. |
| 7,339,585 B2 | 3/2008 | Verstraelen et al. |
| 7,805,177 B2 | 9/2010 | Chen et al. |
| 7,864,997 B2 | 1/2011 | Aben |
| 7,970,187 B2 | 6/2011 | Puts et al. |
| 8,086,000 B2 | 12/2011 | Weijers et al. |
| 8,155,411 B2 | 4/2012 | Hof et al. |
| 8,527,251 B2 | 9/2013 | Ionasec et al. |
| 8,670,943 B2 | 3/2014 | Kassab et al. |
| 8,787,641 B2 | 7/2014 | Hof et al. |
| 8,903,472 B2 | 12/2014 | Kassab |
| 9,119,540 B2 | 9/2015 | Sharma et al. |
| 9,129,418 B2 | 9/2015 | Schormans et al. |
| 9,138,147 B2 | 9/2015 | Schmitt et al. |
| 9,256,936 B2 | 2/2016 | Jacobs et al. |
| 9,265,473 B2 | 2/2016 | Mittal et al. |
| 9,320,487 B2 | 4/2016 | Mittal et al. |
| 9,375,191 B2 | 6/2016 | Verstraelen et al. |

(Continued)

*Primary Examiner* — Ping Y Hsieh
(74) *Attorney, Agent, or Firm* — Medler Ferro Woodhouse & Mills PLLC

(57) ABSTRACT

Systems and methods for determining modified fractional flow reserve values of vascular lesions are provided. Patient physiologic data, including coronary vascular information, is measured. According to the physiologic data, a coronary vascular model is generated. Lesions of interest within the coronary vascular system of the patient are identified for modified fractional flow reserve value determination. The coronary vascular model is modified to generate modified blood flow information for determining the modified fractional flow reserve value.

20 Claims, 7 Drawing Sheets

(56) References Cited

U.S. PATENT DOCUMENTS

| | | |
|---|---|---|
| 9,405,886 B2 | 8/2016 | Taylor et al. |
| 9,538,925 B2 * | 1/2017 | Sharma ................ G16H 50/30 |
| 9,576,360 B2 | 2/2017 | Schormans et al. |
| 9,629,563 B2 | 4/2017 | Sharma et al. |
| 9,700,219 B2 | 7/2017 | Sharma et al. |
| 9,737,276 B2 | 8/2017 | Mittal et al. |
| 9,747,525 B2 | 8/2017 | Sauer et al. |
| 9,757,073 B2 | 9/2017 | Goshen et al. |
| 9,761,048 B2 | 9/2017 | Igarashi |
| 9,775,576 B2 | 10/2017 | Kassab et al. |
| 9,788,807 B2 | 10/2017 | Schmitt et al. |
| 9,811,939 B2 | 11/2017 | Aben et al. |
| 9,842,401 B2 | 12/2017 | Prevrhal et al. |
| 9,867,584 B2 | 1/2018 | Grass et al. |
| 9,888,968 B2 | 2/2018 | Sauer et al. |
| 9,891,044 B2 | 2/2018 | Tu et al. |
| 9,940,736 B2 | 4/2018 | Ishii et al. |
| 9,949,650 B2 | 4/2018 | Edic et al. |
| 9,974,454 B2 | 5/2018 | Sharma et al. |
| 9,974,508 B2 | 5/2018 | Kassab et al. |
| 9,986,938 B2 | 6/2018 | Tu et al. |
| 10,034,614 B2 | 7/2018 | Edic et al. |
| 10,052,031 B2 | 8/2018 | Sharma et al. |
| 10,052,032 B2 | 8/2018 | Grass et al. |
| 10,111,635 B2 | 10/2018 | Kato et al. |
| 10,143,390 B2 | 12/2018 | Ledoux et al. |
| 2013/0132054 A1 | 5/2013 | Sharma et al. |
| 2013/0246034 A1 | 9/2013 | Sharma et al. |
| 2014/0039276 A1 | 2/2014 | Hattangadi et al. |
| 2014/0058715 A1 | 2/2014 | Sharma et al. |
| 2014/0350393 A1 | 11/2014 | Ichihara et al. |
| 2015/0092999 A1 | 4/2015 | Schmitt et al. |
| 2015/0257725 A1 | 9/2015 | Ohishi |
| 2015/0323638 A1 | 11/2015 | Li et al. |
| 2015/0348260 A1 | 12/2015 | Sharma et al. |
| 2015/0374243 A1 | 12/2015 | Itu et al. |
| 2016/0166209 A1 | 6/2016 | Itu et al. |
| 2016/0314581 A1 | 10/2016 | Contini et al. |
| 2016/0321414 A1 | 11/2016 | Salganicoff et al. |
| 2017/0032097 A1 | 2/2017 | Itu et al. |
| 2017/0039736 A1 | 2/2017 | Aben et al. |
| 2017/0046834 A1 | 2/2017 | Itu et al. |
| 2017/0068797 A1 | 3/2017 | Sharma et al. |
| 2017/0071479 A1 | 3/2017 | Kano et al. |
| 2017/0105694 A1 | 4/2017 | Grass et al. |
| 2017/0147778 A1 | 5/2017 | Beurle et al. |
| 2017/0224300 A1 * | 8/2017 | Ishii ....................... A61B 6/469 |
| 2017/0236326 A1 | 8/2017 | Aben et al. |
| 2017/0245821 A1 | 8/2017 | Itu et al. |
| 2017/0258431 A1 * | 9/2017 | Klingenbeck .......... A61B 6/481 |
| 2017/0286628 A1 * | 10/2017 | Shim ..................... G16H 50/50 |
| 2017/0325769 A1 | 11/2017 | Venugopal et al. |
| 2018/0032653 A1 | 2/2018 | Aben et al. |
| 2018/0061047 A1 | 3/2018 | Redel |
| 2018/0082445 A1 | 3/2018 | Ishii et al. |
| 2018/0089829 A1 | 3/2018 | Zhong et al. |
| 2018/0092615 A1 | 4/2018 | Sakaguchi et al. |
| 2018/0211386 A1 | 7/2018 | Ma et al. |
| 2018/0242856 A1 * | 8/2018 | Onozawa ............... G16H 50/50 |
| 2018/0242857 A1 | 8/2018 | Sharma et al. |
| 2018/0253531 A1 | 9/2018 | Sharma et al. |
| 2018/0271468 A1 | 9/2018 | Goshen et al. |
| 2018/0276817 A1 | 9/2018 | Isgum et al. |
| 2018/0286045 A1 * | 10/2018 | Hansis ................... G16H 30/40 |
| 2018/0330507 A1 | 11/2018 | Schormans et al. |

\* cited by examiner

SYSTEM AND METHODS FOR DETERMINING MODIFIED FRACTIONAL FLOW RESERVE VALUES

FIELD OF THE INVENTION

The present invention relates to systems and methods for determining a modified Fractional Flow Reserve value. More particularly, the present invention relates to a systems and methods for modifying Fractional Flow Reserve values based on lesion induced flow rate reductions.

BACKGROUND OF THE INVENTION

The severity of a stenosis or lesion in a blood vessel may be assessed by obtaining proximal and distal pressure measurements relative to the given stenosis and using those measurements for calculating a value of a Fractional Flow Reserve (FFR). FFR is defined as the ratio of a distal pressure $P_d$ measured on a distal side of a stenosis to a proximal pressure $P_a$ measured on a proximal side of the stenosis, typically within the aorta (FFR=$P_d/P_a$). Conventionally, a sensor is placed on a distal portion of a guidewire (FFR wire) to obtain/measure the distal pressure $P_d$, while an external pressure transducer is fluidly connected via tubing to a guide catheter for obtaining the proximal, or aortic (AO) pressure $P_a$. Once the guide catheter is positioned in situ, and the pressure of the blood filling the lumen of the guide catheter is equal to the pressure of the blood at the distal tip of the guide catheter, tubing that fluidly connects the proximal end of the guide catheter to the external pressure transducer also fills with blood such that the external pressure transducer measures the pressure of the blood at the distal tip of the guide catheter, on the proximal side of the lesion. The FFR wire is advanced through the guide catheter and through the lesion to a distal side of the lesion. The sensor on the FFR wire measures the distal pressure.

Calculation of the FFR value provides a stenosis specific index of the functional severity of the stenosis in order to determine whether the blockage limits blood flow within the vessel to an extent that treatment is needed. An optimal or normal value of FFR in a healthy vessel is approximately 1.00, while values less than about 0.80 are generally deemed significant and in need of an interventional treatment. Common interventional treatment options include balloon angioplasty and/or stent implantation.

Conventional methods of FFR measurement, however, do not take into account disruptions and modifications to blood flow rates caused by the presence of the stenosis or lesion, potentially leading to false negative results. Accordingly, there is a need for systems and methods to determine modified FFR values that take into account changes in blood flow caused by the presence of lesions.

BRIEF SUMMARY OF THE INVENTION

Embodiments described herein relate to systems and methods for determining modified FFR values according to blood flow changes due to the presence of blood vessel lesions. The system is configured to model the structure and blood flow of the coronary vasculature of a patient according to obtained physiological data. Lesions of interest that may be clinically significant but have FFR values indicating clinical non-significance are identified within the coronary vasculature. A modified model of the patient's vasculature is then created to estimate blood flow conditions in the absence of a lesion of interest and to determine a modified FFR value based on the estimated blood flow conditions.

In an embodiment, a system for determining modified fractional flow reserve values is provided. The system comprises an angiographic system configured to receive angiographic images of a coronary vascular system; a vascular measurement system configured to receive blood flow measurements of the coronary vascular system; and a computer system including at least one processor configured to execute computer instructions. The computer instructions program the processor to generate a coronary vascular model according to the angiographic images and the blood flow measurements, the coronary vascular model including an arterial tree and a blood flow field describing blood flow and blood pressure, to identify at least one lesion of interest within the coronary vascular model, to generate a modified coronary vascular model according to a removal of the lesion of interest, and to determine a modified fractional flow reserve value for the lesion of interest according to the coronary vascular model and the modified coronary vascular model.

In another embodiment, a computer-implemented method for determining modified fractional flow reserve values is provided and configured to be carried out by at least one processor executing computer instructions. The method comprises receiving, by an angiographic measurement system, angiographic images of a coronary vascular system; receiving, by a vascular measurement system, blood flow measurements of the coronary vascular system; and generating, by the processor, a coronary vascular model according to the angiographic images and the blood flow measurements, the coronary vascular model including an arterial tree and a blood flow field describing blood flow and blood pressure. The method further comprises identifying, by the processor, at least one lesion of interest within the coronary vascular model; generating, by the processor, a modified coronary vascular model according to a removal of the lesion of interest; and determining, by the processor, a modified fractional flow reserve value for the lesion of interest according to the coronary vascular model and the modified coronary vascular model.

DETAILED DESCRIPTION OF THE INVENTION

Figure 1:
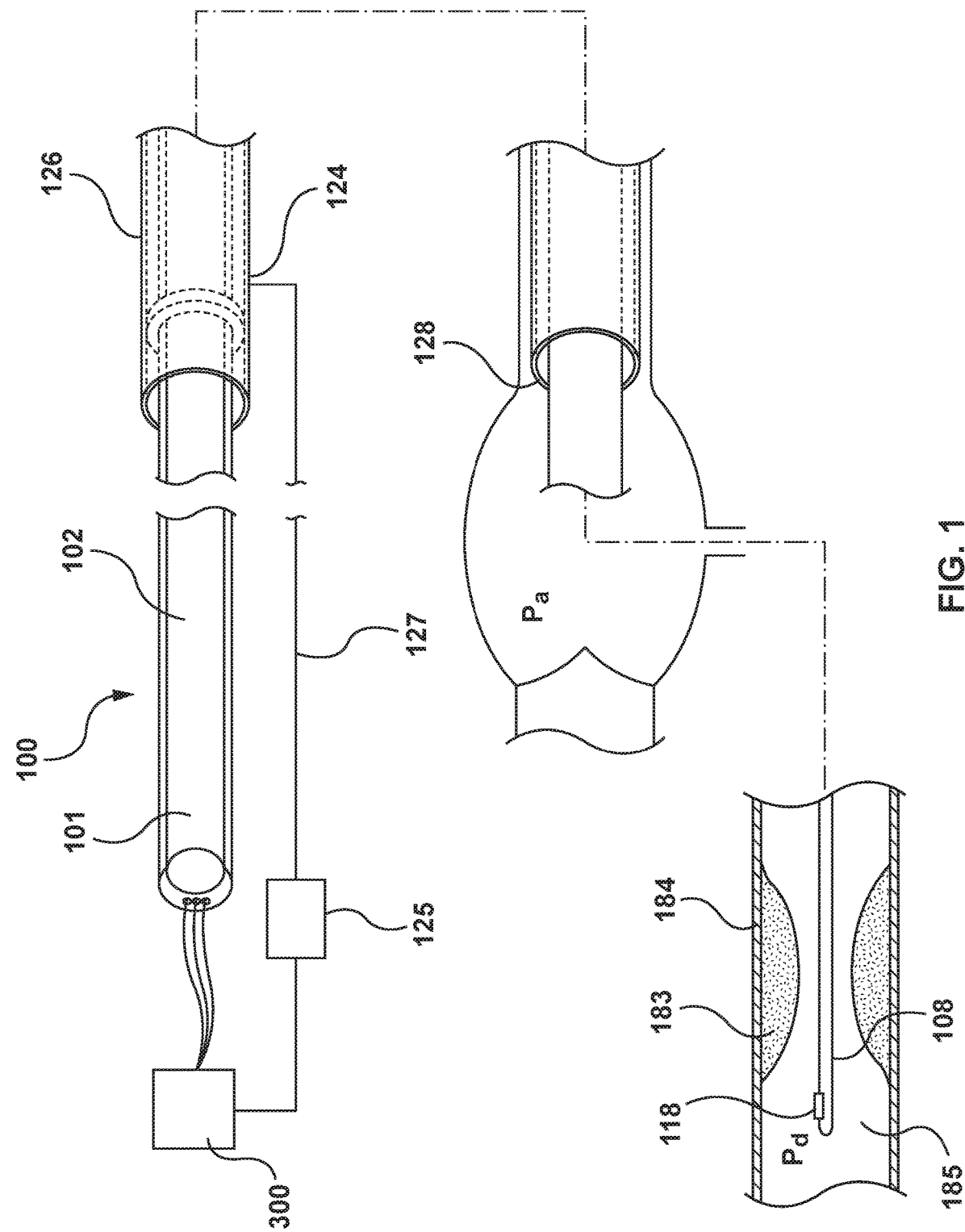
FIG. 1 is a side illustration of a guidewire for measuring an FFR value in accordance with an embodiment hereof.

Specific embodiments of the present invention are now described with reference to the figures, wherein like reference numbers indicate identical or functionally similar elements. The terms "distal" and "proximal", when used in the following description to refer to a catheter, guidewire, or delivery system are with respect to a position or direction relative to the treating clinician. Thus, "distal" and "distally" refer to positions distant from, or in a direction away from the treating clinician, and the terms "proximal" and "proximally" refer to positions near, or in a direction toward the clinician. The terms "distal" and "proximal", when used in the following description to refer to a vessel or a stenosis are used with reference to the direction of blood flow. Thus, "distal" and "distally" refer to positions in a downstream direction with respect to the direction of blood flow, and the terms "proximal" and "proximally" refer to positions in an upstream direction with respect to the direction of blood flow.

The term FFR is used throughout to refer to Fractional Flow Reserve measurements. As used herein, FFR values are defined by a ratio of a distal blood pressure to a proximal blood pressure. FFR values as used herein may be obtained by measurements that are accomplished in situ, i.e., through direct measurement of blood pressures. FFR values as used herein may also refer to FFR values computed or estimated from one or more estimated pressure values, where pressure values are estimated according to modeling techniques discussed herein. FFR values may be computed based on proximal and distal pressure values at any location. For example, an arterial tree specific FFR value may refer to an FFR value taken between a proximal inlet to the arterial tree and a distal vascular location. A vessel branch specific FFR value refers to an FFR value taken at proximal and distal ends of a vessel branch, as defined by locations at which the vessel branch meets a vascular junction. A lesion specific FFR value refers to an FFR value taken between locations close to the proximal and distal ends of a specific lesion.

Although the description and discussion of embodiments herein relate to the determination of a modified FFR value, it is understood that the systems, techniques, and methods described herein may apply to any blood flow or pressure measurement made in an artery having an obstruction. In particular, the systems and methods described herein for FFR values may apply equally to instant wave-free ratio (iFR) values in coronary arteries. Accordingly, all description herein that refers to FFR values may be understood to apply to iFR values and computations as well.

The following detailed description is exemplary in nature and is not intended to limit the invention or the application and uses of the invention. Although the description of the invention is in the context of treatment of blood vessels such as the coronary arteries, the invention may also be used in any other body passageways where it is deemed useful, such as but not limited to peripheral arteries, carotid arteries, renal arteries, and/or venous applications. Furthermore, there is no intention to be bound by any expressed or implied theory presented in the preceding technical field, background, brief summary, or the following detailed description.

FIG. 1 illustrates a pressure measurement system 100 for calculating an FFR value according to an embodiment of the present disclosure. The system 100 includes a guidewire 101 and a guide catheter 126. The guidewire 101 includes a distal portion 108, a proximal portion 102, and at least one pressure sensor 118. The guidewire 101 may further include a hub or handle coupled to a proximal end of the proximal portion 102 for convenient handling of the guidewire 100. In embodiments, the guidewire 101 may be provided without any type of hub or handle. The guidewire 101 is configured to be disposed in a vessel 184 with a proximal end of the proximal portion 102 extending outside of a patient, and the distal 108 positioned in situ within a lumen of the vessel 184 having a lesion or stenosis 183. The guidewire 101 is configured to measure a distal pressure $P_d$ on a distal side 185 of the stenosis 183. Various features of the components of the guidewire system 100 reflected in FIG. 1 and described below may be modified or replaced with different structures and/or mechanisms.

The pressure sensor 118, located on the distal portion 108 of the guidewire 101 measures the distal pressure $P_d$. While an external pressure transducer 125 is fluidly connected via a lumen of the guide catheter 126 for obtaining the proximal, or aortic (AO) pressure $P_a$. Once the guide catheter 126 is positioned in situ, and the pressure of the blood filling the lumen of the guide catheter 126 is equal to the pressure of the blood at the distal tip 128 of the guide catheter 126, tubing 127 that fluidly connects a proximal end 124 of the guide catheter 126 to the external pressure transducer 125 also fills with blood such that the external pressure transducer 125 measures the pressure of the blood at the distal tip 128 of the guide catheter 126. The guidewire 101 is advanced through the guide catheter 126 and through the lesion 183 to a distal side 185 of the lesion 183. The sensor 118 on the guidewire 101 measures the distal pressure $P_d$. The distal pressure $P_d$ and the aortic or proximal pressure $P_a$ are communicated to a computer system, such as computer system 300 described below.

Although FIG. 1 illustrates a system 100 including the pressure sensing guidewire 101 and a guide catheter 126, the systems and methods disclosed herein are compatible with any device capable of measuring or estimating FFR, including systems involving no guide catheter, systems involving FFR catheters, systems that include only a single pressure sensor, and various imaging technologies.

FIGS. 2A-2D illustrate anatomy of a vascular lesion or stenosis and associated blood flows through vessel branches. As used herein, the term "vessel branch" refers to a portion of a blood vessel between vessel bifurcations. A vessel branch is free from bifurcations. An arterial tree is formed of multiple vessel branches having bifurcations between them. In the following discussion of FIGS. 2A-2D, for the purposes of illustration, pressures and flow rates referred to by the same abbreviation are considered to be equal between the different figures. The illustrations of FIGS. 2A-2D are intended to illustrate the effect on blood flow rates and pressures as caused by the presence of lesions. It is understood that other factors, such as vessel diameter, vessel length, vessel wall roughness, etc., may cause changes in pressure and flow rate. For the purposes of example, these factors are not considered in the following discussion.

Figure 2A:
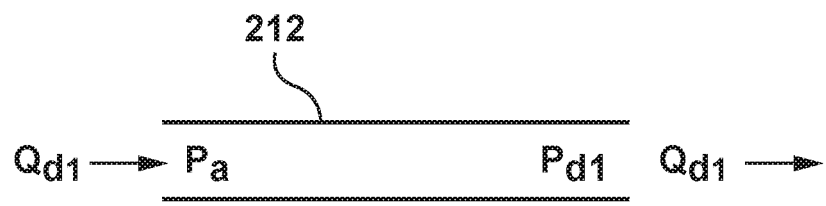
FIGS. 2A-2D illustrate anatomy of a vascular lesion or stenosis and associated blood flows.

FIG. 2A illustrates a lesion free vessel branch 212. The vessel branch 212 has a proximal pressure P_a upstream and a distal pressure P_d1 downstream. Due to the relatively unrestricted flow through the vessel branch, there is a minimal pressure drop between P_a and P_d1. The vessel branch 212 also has a proximal flow rate Q_d1 upstream at an inlet of the vessel branch 212 and a distal flow rate Q_d1 downstream at an outlet of the vessel branch 212. The upstream and downstream flow rates are equal, due to the continuity principle, as all blood flowing into the vessel branch 212 must flow out.

Figure 2B:
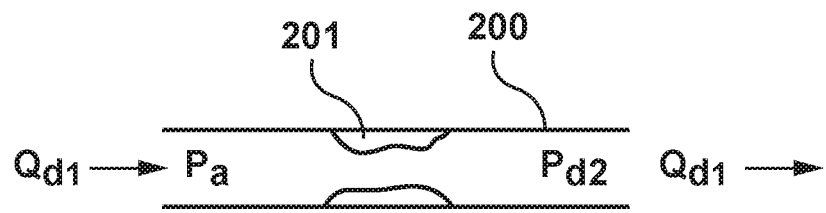

FIG. 2B illustrates a vessel branch 200 having a lesion 201. The vessel branch has a proximal pressure P_a upstream of the lesion 201 and a distal pressure P_d2 downstream of the lesion 201. The vessel branch 200 also has a proximal flow rate Q_d1 upstream of the lesion and a distal flow rate $Q\_d1$ downstream of the lesion. The upstream and downstream flow rates are equal, due to the continuity principle, as all blood flowing into the vessel branch must flow out. The narrowing of the vessel branch 200 at the lesion 201 results in $P\_a$ being higher than $P\_d2$. This pressure difference can be measured or determined by an FFR system and used in the determination of treatment plans. The lesion specific FFR value of the lesion 201 is computed as $P\_d2/P\_a$. In conventional uses of FFR, which is calculated by dividing the downstream pressure $P\_d2$ by the upstream pressure $P\_a$, a score of 0.8 is considered to be the treatment threshold. Lesions scoring less than 0.8 are assessed as lesions to be treated. The 0.8 score indicates a 20% drop in pressure across the lesion.

The pressure drop between any two points in fluid flow is directly related to the volumetric fluid flow rate. An increase in volumetric fluid flow rate results in or requires an increase in pressure drop, while a decrease in volumetric fluid flow rate results in or requires a decrease in pressure drop. That is, larger pressure changes are required to drive larger flows. The exact relationship between volumetric fluid flow rate and pressure drop depends on several factors, such as the flow state of the fluid (e.g., smooth, turbulent, etc.), the diameter of the vessel, the shape of the vessel, the roughness of the vessel walls, and other factors.

Figure 2C:
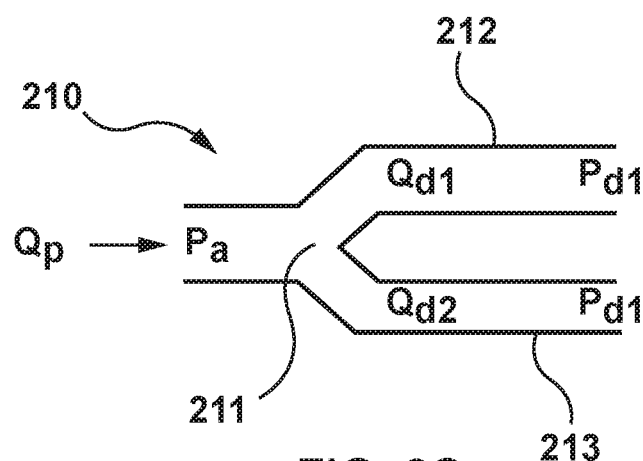

FIG. 2C illustrates a small arterial tree 210 including a bifurcation 211 and two lesion free vessel branches 212 and 213. In the arterial tree 210, the proximal flow $Q\_p$ upstream of the bifurcation 211 splits into two distal flows $Q\_d1$ and $Q\_d2$ through lesion free vessel branches 212, 213 downstream of the bifurcation 211. Due to the continuity principle, the blood flow volume prior to the bifurcation must equal the total blood flow through both branches after the bifurcation. Further, because there are no significant obstructions in either vessel branch 212, 213, the downstream pressure in each, $P\_d3$, is approximately equal. The sum of $Q\_d1$ and $Q\_d2$ equals $Q\_p$. Specific values of $Q\_d1$ and $Q\_d2$ are related to various characteristics of the downstream vessel branches 212, 213 that affect the flow, including size, shape, wall roughness, the presence and nature of lesions, the size and structure of downstream blood vessels, and others. In this structure, with no lesions to cause significant pressure drops, there is minimal pressure drop from the upstream pressure $P\_a$ to the downstream pressure $P\_d1$. Although there may be a slight pressure differential between $P\_a$ and $P\_d1$ as a result of impeded blood flow caused by the bifurcation 211, this differential is insignificant for the illustrative purposes of these examples.

Figure 2D:
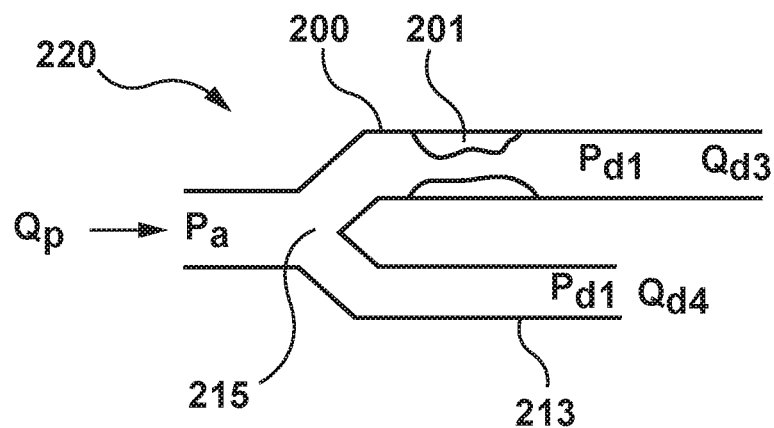

FIG. 2D illustrates an arterial tree 220 having the vessel branch 200 as one of its downstream branches and the lesion free vessel branch 213 as another downstream branch. The lesion free vessel branch 212 of the arterial tee 210 of FIG. 2C is replaced by the vessel branch 200 having lesion 201. For the purposes of illustration, vessel branch 200 is understood to be identical, e.g., in length and diameter, to lesion free vessel branch 212, with the exception of the lesion 201. As discussed above, the lesion 201 restricts blood flow through vessel branch 200, causing a pressure drop from $P\_a$ to $P\_d3$ across the lesion 201. The pressure $P\_d1$ in the lesion free vessel branch 213 is approximately the same as the upstream, or aortic pressure $P\_a$ in the vessel branch 200. As discussed above, the continuity principle requires that the total blood flow prior to the bifurcation 215 be the same as the total blood flow downstream of the bifurcation 215. Accordingly, the upstream, or proximal flow rate $Q\_p$ must equal the sum of the downstream flow rates $Q\_d3$ and $Q\_d4$ in vessel branch 200 and lesion free vessel branch 213, respectively.

Due to the partial flow blockage in vessel branch 200, the flow rate $Q\_d3$ through the vessel branch 200 is reduced as compared to the flow rate $Q\_d1$ through vessel branch 212 in FIG. 2C. This reduction, in turn, requires that the flow rate $Q\_d4$ through vessel branch 213 is increased as compared to the flow rate $Q\_d2$ through vessel branch 213 in FIG. 2C. The total flow rate ($Q\_d3+Q\_d4$) must remain equal to the upstream flow rate $Q\_p$, but the division of flow between the downstream vessel branches 200, 213 changes when the lesion 201 is introduced to the system.

Comparing the vasculature arrangements of FIGS. 2A to 2D, it can be shown that the effects of the bifurcation 215 and lesion 201 combine to create a reduced FFR score for the lesion 201 in the arterial tree 220 as compared to the vessel branch 200 with no bifurcation 215. As discussed above, the addition of the lesion 201 to the arterial tree 220 including the bifurcation 215 causes blood flow to shift to the lesion free vessel 213. The pressure drop across lesion 201 is directly affected by the blood flow rate through the lesion. Thus, the pressure drop across lesion 201 in the arterial tree 220, where the blood flow rate $Q\_d3$ is reduced in comparison to the blood flow rate $Q\_d1$, is reduced compared to the pressure drop across lesion 201 in the structure of FIG. 2B containing no bifurcation. The shift in blood flow from the partially obstructed vessel branch 200 to the lesion free vessel branch 213 moderates the pressure drop across the lesion 201 and serves to increase the FFR value of the lesion 201 inside the arterial tree 220. This moderation in the pressure drop and increase in the FFR value may serve to obscure the clinical dangers that a particular lesion presents to a patient.

Figure 3:
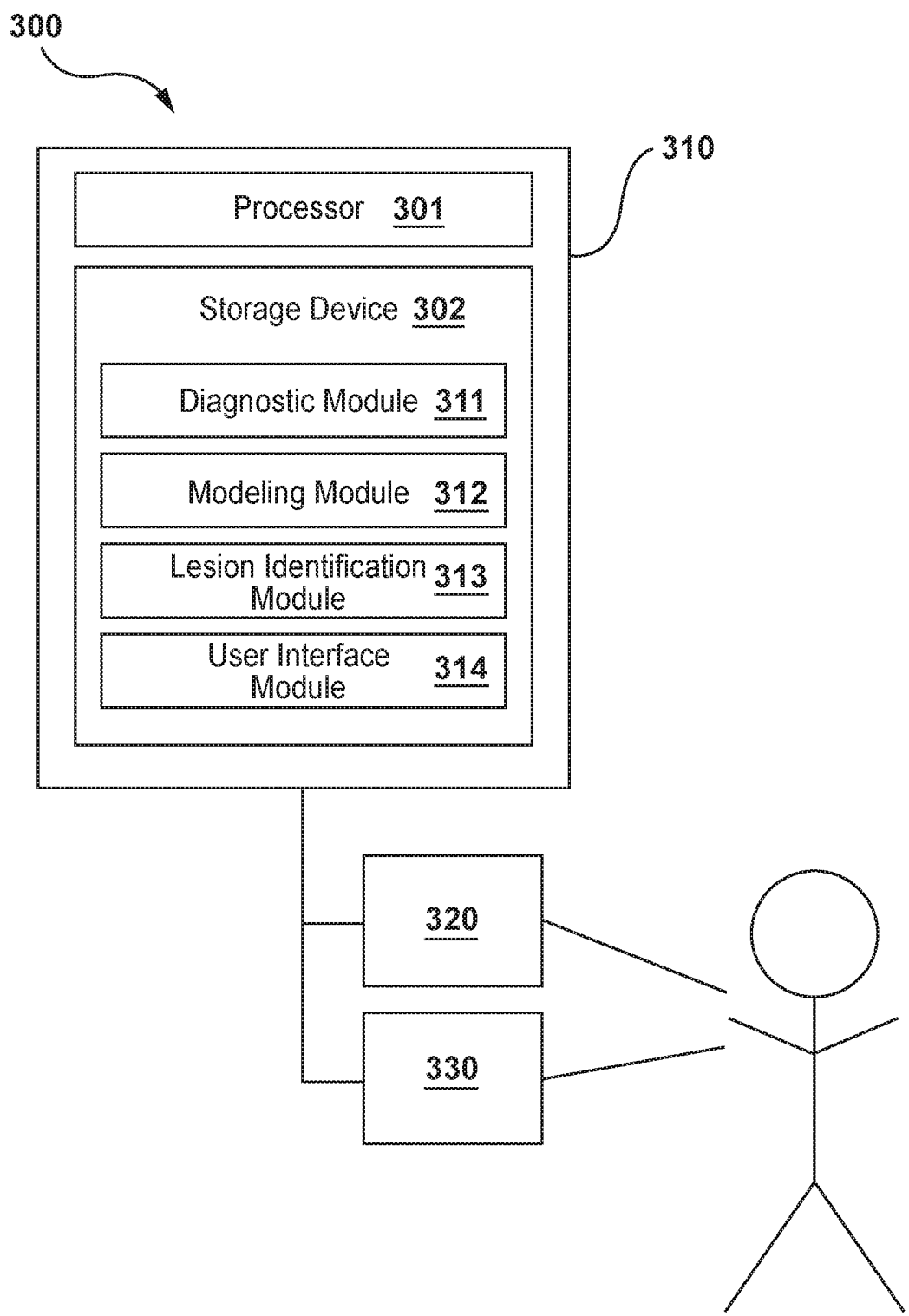
FIG. 3 illustrates a system for the determination of modified FFR values in accordance with embodiments hereof.

FIG. 3 illustrates a schematic of a system for determining modified FFR values. The system 300 includes one or more of a computer system 310, a vascular measurement system 320, and an angiographic measurement system 330. The computer system 310 includes one or more processing modules, including a diagnostic module 311, a modeling module 312, a lesion identification module 313, and a user interface module 314.

Although illustrated in FIG. 3 as including several components, the system 300 may include more or fewer components than those described, connected and/or communicating in ways different than those described. For example, the computer system 310 is configured to receive physiologic data, as discussed further below, from the vascular measurement system 320 and the angiographic measurement system 330. In embodiments, the computer system 310 may receive equivalent physiologic data from any system or device capable of obtaining the required data. In embodiments, the computer system 310 may receive the physiologic data directly from the vascular measurement system 320 and angiographic measurement system 330. In further embodiments, the computer system 310 may access data obtained by such systems and stored on a computer memory. In further embodiments, all or a portion of the capabilities and functionality of any of the components of the system 300 may be carried out by other components of the system 300.

The computer system 310 may be configured as a server (e.g., having one or more server blades, processors, etc.), a personal computer (e.g., a desktop computer, a laptop computer, etc.), a smartphone, a tablet computing device, and/or other device that can be programmed to receive and output data and to interact with an operator. In an embodiment, any or all of the functionality of the computer system may be performed as part of a cloud computing platform.

The computer system 310 includes one or more processors 301 (also interchangeably referred to herein as processors 301, processor(s) 301, or processor 301 for convenience), one or more storage device(s) 302, and any input and output components such as displays, speakers, mice, keyboards, Wi-Fi antennas, communications ports, etc., required for operation. The processor 301 is programmed by one or more computer program instructions stored on the storage device 302. For example, the processor 301 is programmed by a diagnostic module 311, a modeling module 312, a lesion identification module 313, and a user interface module 314, the software instructions for which are stored on the storage device 302. As used herein, for convenience, the various instruction modules and systems will be described as performing an operation, when, in fact, the modules and systems program the processor 301 (and therefore the computer system 310) to perform the operation.

The vascular measurement system 320 includes one or more vascular measurement devices and any associated or required software, hardware, and/or other components required to obtain, receive, or measure physiologic data of a patient as described herein. The vascular measurement system 320 is configured to obtain blood flow measurements, e.g., physiologic data about one or both of blood flow velocity and vascular blood pressure. To make such measurements, the vascular measurement system 320 may include pressure wires or catheters as well as devices for determining blood flow velocities. In embodiments, the vascular measurement system 320 may include an FFR measurement system such as the system 100 as described with respect to FIG. 1.

The angiographic system 330 is configured to obtain or receive angiographic imaging data, in the form of angiographic images, of a patient and includes systems and devices for collecting such angiographic data of the patient, along with any associated hardware and software. Suitable systems may include those capable of angiographic imaging via fluoroscopy, Computed Tomography (CT), and Magnetic Resonance Imaging (MRI). The angiographic system 330 is configured to inject the patient with radio-opaque contrast fluid and use imaging techniques to image the coronary vasculature and the rate of contrast fluid clearance. In embodiments, multiple images or slices may be obtained to generate a three-dimensional image of the coronary vasculature. In additional embodiments, other coronary imaging systems, such as radionuclide angiography systems may be used in place of the angiographic system 330.

The diagnostic module 311 is a software module in operation on the computer system 310. The diagnostic module 311 is configured to collect, obtain, or otherwise receive patient physiologic data describing the coronary vascular system, including at least blood flow measurements and angiographic images. The diagnostic module 311 may be configured to receive and interpret patient physiologic data directly from the vascular measurement system 320 and the angiographic system 330. The diagnostic module 311 may further be configured to obtain patient physiologic data from a storage location. The diagnostic module 311 may further be configured to receive patient physiologic data at any level of processing, from direct raw data such as angiographic images and pressure measurements, to processed data that has previously been refined and analyzed. The diagnostic module 311 is further configured to communicate with the modeling module 312 to provide the modeling module 312 with the required data. In embodiments, the diagnostic module 311 is configured to operate as the vascular measurement system to receive coronary vascular blood flow measurements. In embodiments, the diagnostic module 311 is configured to operate as the angiographic system to receive angiographic images of the coronary vascular system. Further features and operations of the diagnostic module 311 are discussed below with respect to the operational processes of FIGS. 4 and 5.

The modeling module 312 is a software module in operation on the computer system 310. The modeling module 312 is configured to construct and modify patient coronary vascular models. The modeling module 312 is configured to generate a coronary vascular model according to the angiographic images and the blood flow measurements. The coronary vascular model generated by the modeling module 312 includes information describing coronary vascular structure and coronary vascular blood flow of the patient coronary vascular system. The modeling module 312 is further configured to generate a modified coronary vascular model and, based on the original coronary vascular model and the modified coronary vascular model, determine modified FFR values of lesions of interest. Further features and operations of the modeling module 312 are discussed below with respect to the operational processes of FIGS. 4 and 5.

The lesion identification module 313 is a software module in operation on the computer system 310. The lesion identification module 314 is configured to identify lesions within the patient coronary vasculature according to the patient physiologic data, including both the angiographic images and the blood flow measurements. The lesion identification module 314 is further configured to identify lesions of interest within the patient coronary vasculature according to the patient physiologic data, including both the angiographic images and the blood flow measurements. A lesion of interest is a lesion that is not identified as clinically significant under standard FFR guidelines (i.e., because it has an FFR value greater than 0.8) but appearing to a physician, other analyst, or the system 300 as requiring further analysis. Further features and operations of the lesion identification module 313 are discussed below with respect to the operational processes of FIGS. 4 and 5.

The user interface module 314 is a software module in operation on the computer system 310. The user interface module 314 is configured to receive user input, provide user output, and otherwise provide all necessary components and features to facilitate user interaction with the computer system 310. The user interface module 314 may be configured to receive and output information to and from any number of user input/output devices, including mice, keyboards, touchscreens, displays, speakers, and others. Further features and operations of the user interface module 314 are discussed below with respect to the operational processes carried out.

Figure 4:
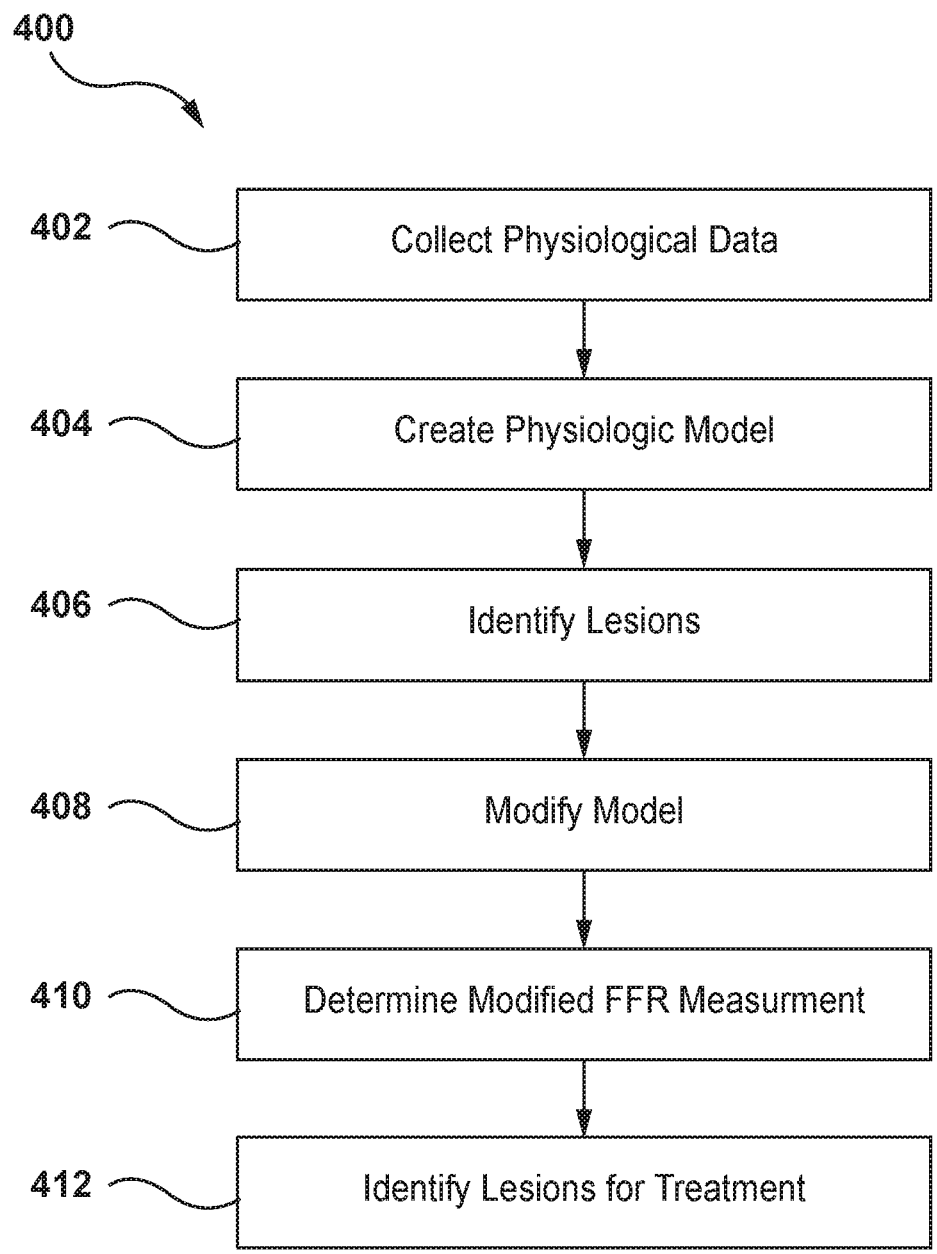
FIG. 4 is a flowchart depicting a process for determining a modified FFR value.

FIG. 4 illustrates a modified FFR value determination process 400 according to embodiments hereof. As discussed above with respect to FIG. 2, shifts in blood flow caused by the presence of a lesion in a blood vessel that is part of a larger arterial tree may cause an increased measured FFR value with respect to the same blood vessel and lesion in an isolated scenario. The modified FFR value determination process 400 serves to determine a modified FFR value that accounts for this increase in measured FFR when a measured blood vessel is part of a larger arterial tree or vascular network. The modified FFR value determination process 400 includes a series of operations for anatomical modeling based on measured blood flows and velocities, identification of potentially treatable lesions, and model modification to determine modified FFR values of the treated lesions. The operations of the process 400 may be implemented by components of the system 300, including the computer system 310, the vascular measurement system 320, and the angiographic measurement system 330. Other hardware or components may be used to carry out the various operations of the process 400 as discussed below, and the description of hardware and components herein is intended as an example and not a limitation.

In an operation 402, physiologic data of a patient is collected. The collected physiologic data includes at least patient vascular data and may further include any data relevant to a patient's treatment. Patient vascular data is data describing a patient's vascular system. In particular, patient vascular data includes data describing a patient's coronary vascular network. Patient vascular data includes at least information about blood pressures, blood flow rates and velocities, and vascular structure including blood vessel geometry, locations, and branches. In embodiments, collection of physiologic data may be assisted by the diagnostic module 311.

The diagnostic module 311 is configured to interface with the angiographic measurement system 330 and/or the vascular measurement system 320. The diagnostic module 311 may communicate with, send instructions to, and/or receive information from the angiographic measurement system 330 and/or the vascular measurement system 320. In embodiments, physiologic data collection performed by the angiographic measurement system 330 and/or the vascular measurement system 320 may be performed under the control of the diagnostic module 311. In additional embodiments, an operator may operate the angiographic measurement system 330 and the vascular measurement system 320 independently and transfer recorded data to the computer system 310 under control of the diagnostic module 311. The physiologic data collection operation 402 is described in greater detail with respect to FIG. 5.

Figure 5:
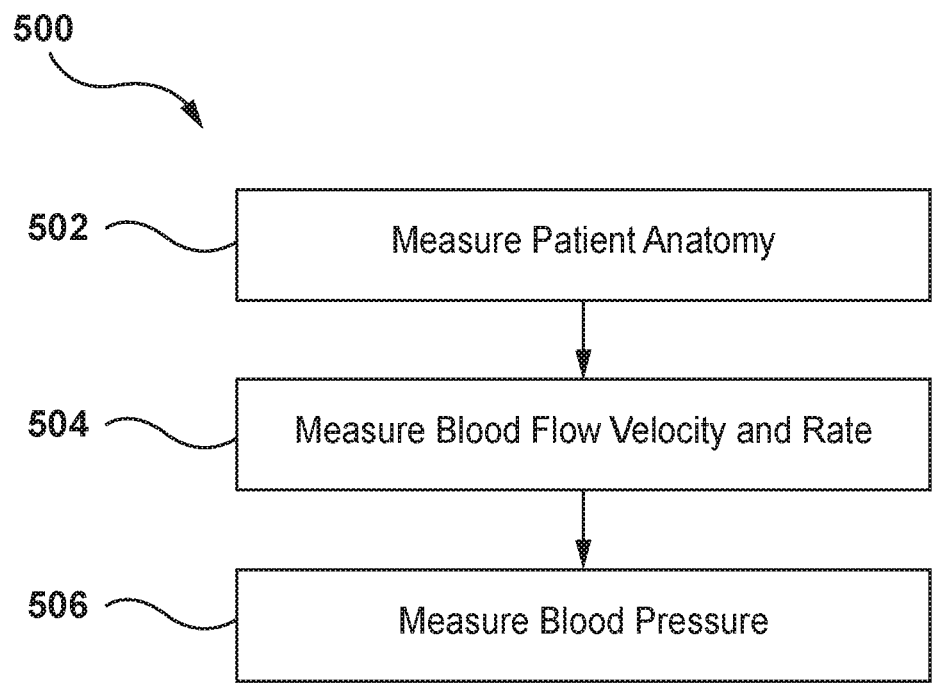
FIG. 5 is a flowchart depicting a process of obtaining patient physiologic data.

FIG. 5 is a flow diagram illustrating a physiologic data collection process 500 consistent with embodiments hereof. Physiologic data collection process 500 may be implemented to collect patient vascular data. The process 500 gathers required data to describe the patient baseline vascular anatomy as used for subsequent modeling. As used herein, the baseline vascular anatomy refers to the measured patient anatomy and blood flow measurements prior to any clinical intervention. Physiologic data collection processes consistent with embodiments hereof may include any combination of the operations of the process 500 as described with respect to FIG. 5, including combinations that do not include all of the described operations and including combinations that include the described operations conducted in any order.

In an operation 502, the physiologic data collection process 500 includes measuring patient anatomy. The coronary vascular structure of the patient is measured to generate a coronary map of the patient, including a map of the coronary vascular network and the size of the blood vessels at each point in the vascular network. The coronary map may include a three dimensional map generated through the use of multi-image angiography. Any suitable angiographic technique, including those using fluoroscopy, CT, and MRI, may be applied to capture the patient coronary map. In further embodiments, a CT scan may be used to generate the patient coronary map.

In an operation 504, the physiologic data collection process 500 includes measuring blood velocity and flow throughout the patient coronary vascular network. A plurality of blood flow measurements at different locations may be made to determine blood flow velocity at each of the different locations. Repeated measurements throughout the vasculature are used to generate a blood flow field describing the blood flow and blood pressure. In an embodiment, a flow wire that measures velocity at the distal tip of the wire is used to make blood flow velocity measurement. In additional embodiments, the blood flow velocity throughout the vasculature may be estimated based on the rate at which contrast fluid is cleared. Both the vascular measurement system 320 and the angiographic measurement system 330 may be used in operation 504.

In an operation 506, the physiologic data collection process 500 includes measuring pressure throughout the patient coronary vascular network. Pressure measurements may be performed through the use an FFR pressure wire or catheter as described herein and/or by any other suitable device for measuring intravascular blood pressure. Pressure measurements conducted at operation 506 provide information about pressure at measured locations of the vascular network. Measurements taken by the FFR system can be used to generate a patient coronary vascular network pressure field. The FFR system may also be used to determine FFR scores of known lesions within the patient's vascular network.

Returning now to FIG. 4, in an operation 404 a physiologic model is generated according to the measured physiologic data. The measured physiologic data, as received and processed by the diagnostic module 311, is transmitted to the modeling module 312 for model generation at operation 404. The modeling module 312 is configured to construct a patient coronary vascular model according to the received physiologic data.

Figure 6:
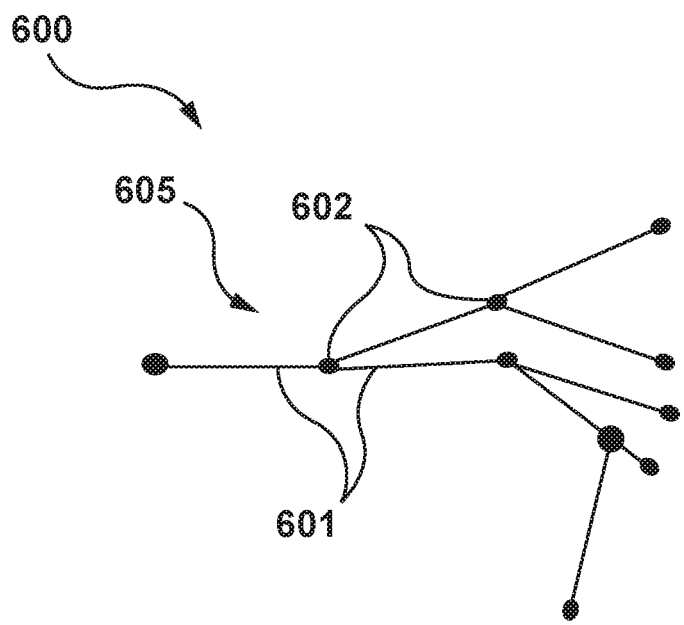
FIG. 6 is a diagram illustrating a blood flow network model.

In embodiments, the modeling module 312 is configured to generate a blood flow network model according to the received physiologic data. FIG. 6 is a diagram illustrating a blood flow network model 600. The network model 600 is a model describing the coronary vascular structure and the blood flows according to a network graph. The network model 600 stores information about an arterial tree 605, including each vessel branch 601 in the network and the vessel branch nodes 602. The network model 600 also stores a blood flow field, including information about the blood pressures and blood flow rates at one or more locations within the vessel branches. As illustrated in FIG. 6, the network model 600 includes a plurality of vessel branches 601 and nodes 602. Each vessel branch 601 includes two nodes 602. The pressures and blood flow rates for each of the plurality of vessel branches 601 are stored in the network model 600. In embodiments, the network model 600 includes proximal and distal measurements or estimates of blood pressure and blood flow rate. In embodiments, the network model 600 includes three or more blood pressure and blood flow rate values. For vessel branches 601 where blood pressure and flow were measured during operation 402, the measurements are stored in the network model 600.

For vessel branches 601 where blood pressure and flow were not measured, modeling module 312 is configured to estimate blood flow and blood pressure values according to existing measurements based on principles that govern the network model 600. For example, the network model 600 requires that the continuity principle be maintained. Blood flows in to and out of any vessel branch node 602 must be equal. In another example, differences in blood pressures at adjacent nodes 602 may be determined according to pressure change causing features (including, for example, vessel diameter changes, lesion presence, vessel wall friction, vessel length, vessel geometry, and vessel junction geometry) of a vessel branch 601 extending between them. Accordingly, each vessel branch 601 of the network model 600 is characterized by proximal and distal blood pressure and blood flow measurements, and by two vessel branch nodes 602.

In embodiments, the modeling module 312 is configured to generate the network model 600 according to the patient vascular data, including angiographic imaging data describing the coronary structure and measured blood flow rates, velocities, and blood pressures. Although the network graph of network model 600 is described with specific requirements, variations in the network graph, including additional blood flow and pressure measurements and/or additional or different linking requirements between vessel branches 601 and vessel branch nodes 602 may be used.

Figure 7A:
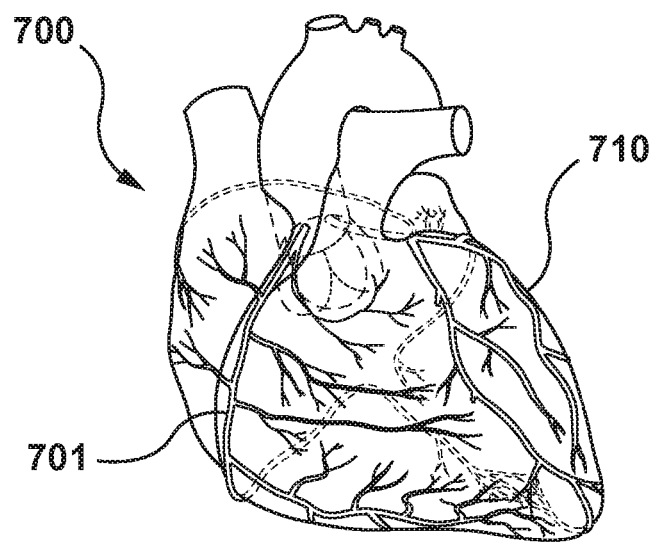
FIGS. 7A-7D illustrate aspects of a blood flow computational model.
Figure 7B:
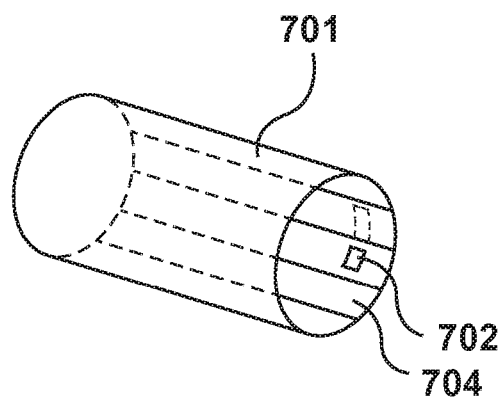
Figure 7C:
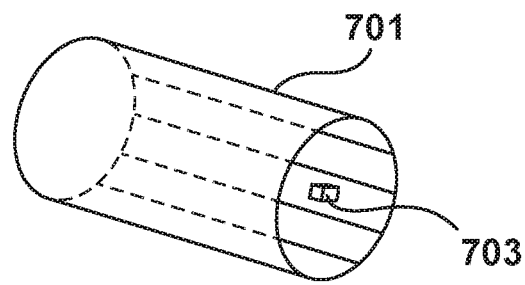

In embodiments, the modeling module 312 is configured to generate a computational model according to the received physiologic data. FIGS. 7A-7C illustrate aspects of a computational model 700. The computational model 700 is a blood flow model including an arterial tree 710 containing information about the coronary vascular structure according to an anatomical model and a blood flow field including information about blood flow rates and blood pressures and blood flows throughout the coronary vascular structure. The computational model 700 is a model suitable for use with finite element analysis (FEA) techniques, software, and methods.

FIG. 7A illustrates the arterial tree 710, the branching network of coronary blood vessels that define the coronary vasculature. As discussed above, images of the coronary vasculature are captured during the physiologic measurement operation 504. The measured physiologic data, e.g., the angiographic images, are converted, if necessary, into digital form. Image capture and interpretation is employed to digitally define the arterial lumens of the coronary vascular network. The arterial lumens of the blood vessels are each defined by a series of three-dimensional coordinates defining the arterial wall. FIG. 7B illustrates a wall element 702 on the interior arterial wall 704 of a coronary blood vessel 701. The wall element 702 is defined by three-dimensional coordinates. In embodiments using a rectilinear coordinate scheme, each wall element 702 is defined by x, y, z coordinates. Each wall element 702 borders a neighboring wall element 702, with the size of the wall elements 702 being based on a desired resolution of the computational model 700. The blood vessel 701 is further defined by a plurality of wall elements 702 spread across the entirety of the arterial wall 704. The rest of the arterial tree 710 is similarly defined by a plurality of wall locations 702 spread throughout the entirety of the vascular network.

FIG. 7B illustrates an interior element 703 of the blood vessel 701. Each interior element 703 is defined by three-dimensional coordinates, and the entire interior of the blood vessel 701 is defined by a plurality of interior elements 703. In embodiments using a rectilinear coordinate scheme, each interior element 703 is defined by x, y, z coordinates. Each vessel 701 of the arterial tree 710 may be defined by a plurality of interior elements 703 such that the entirety of the arterial tree 710 is defined.

The blood flow velocity or flow rate data gathered at operation 504 may then be used to construct a velocity field for the arterial tree 710. According to measurements obtained at operation 504, the blood flow rate at various locations within the blood vessels 701 is known. Based on the modeled assumptions regarding the flow rate in the blood vessels, such as a parabolic local velocity field in the case of laminar flow, the blood flow velocity can be determined and assigned to the interior elements 703 as an additional variable (x, y, z, v). The modeling module 312 is configured to determine the blood flow velocities according to the measured physiologic data. Blood flow velocities may be determined for all or some of the interior elements 703.

Where the measured physiologic data obtained at operation 504 includes pressure data, then a pressure field throughout the arterial tree 710 is constructed as well. In the case of laminar flow in a tube, pressure only varies along the length of the tube, so all points in the same cross-section have the same pressure value. Pressure in a given cross-section is determined and each point in that cross-section is assigned an additional variable p, so that each interior element 703 is defined by the variables: (x, y, z, v, p). The modeling module 312 is configured to determine blood pressures throughout the arterial tree 710 according to the measured physiologic data. Blood pressures may be determined for all or some of the interior elements 703.

Physiologic data determined at operation 402 may not be sufficient to determine blood pressure and velocity at the location of every single interior element 703 within the computational model 700. In further embodiments, FEA techniques may be employed to generate pressure and velocity values of any interior element 703 for which it is not measured directly. FEA is a computational approach that finds an approximate solution to the problem under study according to governing rules and boundary conditions. The accuracy of the final result is improved by looking at the problem in finer and finer scale, i.e., by making the elements such as interior elements 703 and wall elements 702 smaller. Such accuracy comes at the expense of additional computational time or resources required.

The FEA computational solution for generating computational model 700 requires several inputs. The first required input is the domain. The domain is defined by the arterial tree 710 and the interior elements 703 and wall elements 702 that define it. Accordingly, the modeling module 312 may generate the computation model 700 domain according to physiologic data describing the arterial tree 710, or coronary vascular network.

Figure 7D:
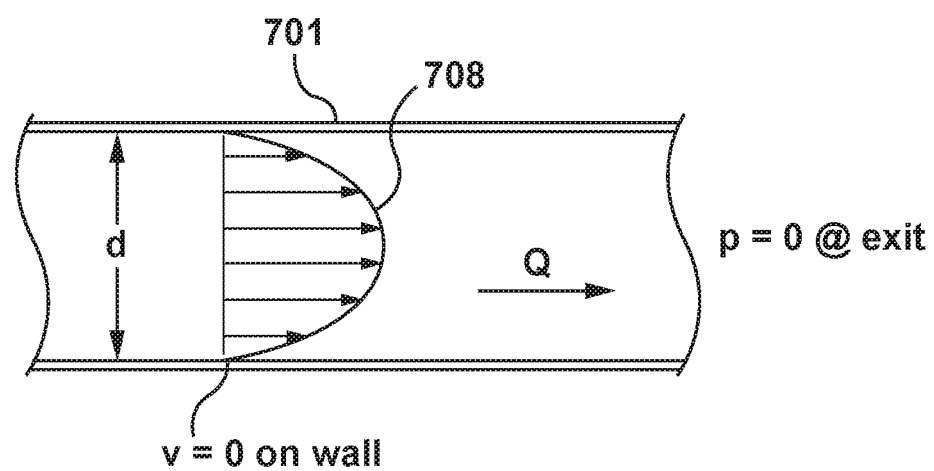

Another required input is boundary conditions. The modeling module 312 may be configured to generate the computational model 700 according to boundary conditions. The boundary conditions constrain the FEA computations by providing restricted results at specific interior elements 703. For example, a no-slip boundary condition might be applied to the vessel wall, requiring that, at any point on the wall, the blood flow velocity is set to zero. For any interior element 703 located adjacent to the lumen wall, the variables become (x, y, z, 0, p), with the velocity being set at zero. This boundary condition is illustrated at FIG. 7D, which illustrates a velocity profile 708 through blood vessel 701 having a velocity of 0 adjacent to the vessel wall. Another example boundary condition includes the addition of known data. Thus, the pressures and flow rates obtained during operation 402 are included for all interior elements 703 to which they apply. In another example boundary condition, the measured volumetric flow rate throughout the arterial tree 710 may be used to establish a velocity profile spanning several interior elements 703 at the inlet to the domain. In this case the inlet to the domain, or the arterial tree 710, might be the cross-section of the arterial tree at the opening of the left main artery. For example, a parabolic velocity profile would be chosen that when integrated across the vessel area yields the measured flow-rate. By maintaining the inlet velocity profile boundary condition as a constant throughout the computational process, all calculations are constrained to the correct volume flow rate throughout the entirety of the arterial tree 710 domain. Further boundary conditions may include boundary conditions establishing a datum or baseline for the pressure field. For example, the pressure value at a single point at the exit from the arterial tree 710 domain in one of the distal vessels 701 of the arterial tree 710 may be constrained to 0.

Another required input is a set of governing equations. The modeling module 312 is configured to generate the computational model 700 according to governing equations. In the simplest case of a Newtonian fluid, there are two variables (velocity and pressure). Accordingly, two governing equations are needed to avoid over constraint or under definition of the FEA problem-space. For example, governing equations that describe conservation of mass and conservation of momentum may be used. In tensor form these may be written as:

Conservation of mass: $\nabla \cdot v = 0$

Conservation of momentum $\mu \nabla^2 v + \nabla p = 0$ where v is the velocity vector, p is pressure and μ is a material property of the fluid called viscosity.

The modeling module 312 is configured to generate, using FEA techniques, the computational model 700 of the patient coronary vascular using a domain, boundary conditions, and governing equations consistent with the above discussion. For the FEA computation, the arterial tree 710 domain is divided into interior elements 703, and, within each element, the variables of interest are approximated with simple polynomial functions. For example, the velocity may be approximated within each element using a quadratic polynomial function and the pressure with a linear polynomial function. The polynomial functions are constrained to be continuous across element boundaries. There can be no discontinuities or step changes in the function. The goal of FEA is to establish the size and shape of each of the local polynomial functions by determining the individual polynomial parameters for every local polynomial function. The FEA output is a set of polynomial parameters for every local polynomial function. These output parameter values are calculated to be the best fit to the requirements established across the entire domain. That is, the FEA solution honors the boundary conditions and meets the requirements of the governing equations in a best fit manner.

The modeling module 312 is configured to perform the FEA computations throughout the arterial tree 710 domain to establish blood flow and pressure throughout every location within the coronary vasculature. As discussed above, increasing the precision and resolution of the FEA computations may create a strain on computational resources. Accordingly, the modeling module 312 may be configured, in embodiments, to generate the computational model 700 to define only a portion of the patient vasculature. The FEA computations and inputs may be adjusted accordingly to achieve a computational model 700 defining a portion of the patient vasculature.

Returning now to FIG. 4, in an operation 406 of process 400, vascular lesions are identified. A portion of the identified vascular lesions are further identified as lesions of interest. The lesion identification module 413 is configured to identify vascular lesions and lesions of interest, as described below. Vascular lesions include all lesions, or any size or shape, within the patient coronary vasculature. Lesions of interest include any vascular lesions for which a physician or other operator wishes to obtain more information and/or any vascular lesion that meets specific predetermined criteria. For example, a lesion of interest is a lesion that is not identified as clinically significant under standard FFR guidelines (i.e., because it has an FFR value greater than 0.8) but appearing to a physician, other analyst, or the system 300 as requiring further analysis. Lesions and lesions of interest may be identified via several analysis techniques using the data and models obtained from earlier steps. The following analysis techniques may be combined in any manner without departing from the scope of the invention. For example, multiple identification techniques may be used in identifying lesions and lesions of interest to create redundancy. In another example, one or more techniques may be used to identify lesions while one or more techniques that may differ are used to identify lesions of interest.

The following lesion identification techniques may be performed by an operator, such as a physician, automatically through computation, or a combination of both. For example, the lesion identification module 313 may identify all vascular lesions and display these to the operator via the user interface module 314. The operator may then select lesions of interest from among the identified vascular lesions. Display of the vascular lesions may include display of any analysis information obtained from the analysis techniques discussed below, such as imaging data and/or FFR data. The analysis information may be used by the operator to select lesions of interest. In another example, the lesion identification module 313 may identify lesions of interest through computation alone based on predetermined criteria. In yet another example, the lesion identification module 313 may identify potential lesions of interest according to predetermined criteria and then request operator verification and approval of each potential lesion of interest.

The techniques and models discussed below for identifying lesions and lesions of interest represent an array of tools available to an operator of the computer system 310 and to the computational capabilities of the computer system 310. The tools and techniques discussed may be used in any combination with or without operator intervention. The discussion of specific combinations is intended for example purposes only and is not intended as limiting with respect to specific combinations that are not discussed.

In an embodiment, lesions are identified by the lesion identification module 313 according to imaging analysis. Based on the imaging obtained during the physiologic data collection steps, an operator or image analysis software may identify lesions within the coronary vasculature. Image analysis may further be used to select one or more lesions of interest for further study. In further embodiments, image analysis software may be used to identify lesions of interest within the imaging data.

In a further embodiment, lesions are identified according to FFR values determined from pressure measurements taken during physiologic data collection operation 504. FFR values used to identify lesions and lesions of interest may be arterial tree specific, vessel branch specific, and or lesion specific. FFR values from the physiologic data collection may include any comparison of measured proximal and distal pressures, whether the measurements were made concurrently or not, with an FFR catheter or not, or otherwise. FFR values of less than 1, i.e., any FFR value indicating an obstruction of flow, may be used to identify a vascular lesion. Lesions of interest are also identified according to FFR values obtained according to data collected during the physiologic data collection operation 402. Lesions of interest are identified according to FFR value criteria. Accordingly, an FFR range may be used as the FFR value criteria to identify lesions in some embodiments. For example, an FFR range between 0.95 and 0.8 may be used to identify lesions of interest. Lesions with measurements greater than 0.95 may not be significant enough to warrant further investigation while lesions with measurements below 0.8 may already be established as clinically significant based on standard guidelines. Different FFR ranges may be used as required.

In embodiments, lesions and lesions of interest may be identified according to the vascular network model 600. The vascular network model 600 includes proximal and distal pressure data points throughout the vasculature. As discussed above, the data points may be a mix of measured and estimated pressures. The proximal and distal pressure data points may be used to compute FFR values between any two points within the network model 600. FFR values used to identify lesions and lesions of interest may be arterial tree specific, vessel branch specific, and or lesion specific, depending on the data available within the network model 600. The network model 600 FFR values may be used to identify lesions through FFR values less than one. Lesions of interest are identified according to FFR value criteria. Accordingly, an FFR range, e.g., between 0.95 and 0.8, may be used as the FFR value criteria to identify lesions in some embodiments. Other FFR ranges may be used as necessary. In embodiments, lesions and lesions of interest identified through use of the network model 600 may be confirmed via imaging or other technique. In embodiments, the presence of lesions may be identified based on arterial tree specific FFR values and the identification of lesions of interest may be performed based on branch specific or lesion specific FFR values.

In embodiments, lesions and lesions of interest may be identified according to the computational model 700. The computational model 700 includes interior elements 703 storing pressure data throughout the vasculature. Any two interior elements 703 within the arterial tree 710 may be used to compute an FFR based on a pressure drop between them. The pressure data of the interior elements 703 may be used both to identify lesions and identify lesions of interest according to FFR computations. In embodiments, FFR may be computed with respect to the pressure at the inlet to the arterial tree. Thus, the downstream pressure at any location in the tree may be compared to the inlet pressure in an arterial tree FFR value. The arterial tree specific FFR value may be used to identify lesions based on downstream pressure measurements that show a significant drop in pressure. In further embodiments, FFR values may be computed with respect to specific blood vessels or lesions. Because the pressure drop within an unobstructed vessel branch is relatively low, a branch specific FFR computed based on pressure measurements at the proximal and distal ends of the branch in the case that the branch includes one lesion will be approximately the same as an FFR computed based on pressure measurements immediately upstream and immediately downstream of a lesion. If the branch includes more than one lesion, the branch specific FFR will differ from the lesion specific FFRs or each lesion.

Lesions of interest are identified from among the lesions according to FFR value criteria. Accordingly, an FFR range may be used as the FFR value criteria to identify lesions in some embodiments. The appropriate FFR range may be adjusted according to the specific FFR value used (e.g., arterial tree specific, branch specific, lesion specific). In embodiments, the FFR range may be a range between 0.95 and 0.8 or other range found to be appropriate. In embodiments, lesions and lesions of interest identified through use of the computational model 700 may be confirmed via imaging or other technique. In embodiments, the presence of lesions may be identified based on arterial tree specific FFR values and the identification of lesions of interest may be performed based on branch specific or lesion specific FFR values.

In an operation 408 of process 400, the modeling module 312 is employed to modify the vascular model according to the lesion of interest selection. Any of the exemplary models, including the network model 600 and the computational model 700 may be modified by the modeling module 312 according to the following.

The modeling module 312 is configured to modify the vascular model by reconstructing the model without the presence of one or more lesions of interest. For example, the modeling module may remove a single lesion of interest from the vascular model and compute the modified vascular model based on the removal. The modeling module 312 is configured to estimate or compute modified blood pressures and flows in the modified vascular model based on the removal of the lesion of interest.

In the network model 600, removal of a lesion of interest by the modeling module 312 may be performed by setting the proximal and distal pressures of the vessel branch 601 which contains the lesion of interest to be equal. Thus, instead of showing a pressure drop across the length of the vessel branch where the lesion of interest was, the modified network model 600 shows no pressure drop. Blood flows and pressures may then be redetermined throughout the modified network model 600 according to the adjusted pressure in the lesion of interest containing vessel according to the governing principles of the network model 600.

Figure 8A:
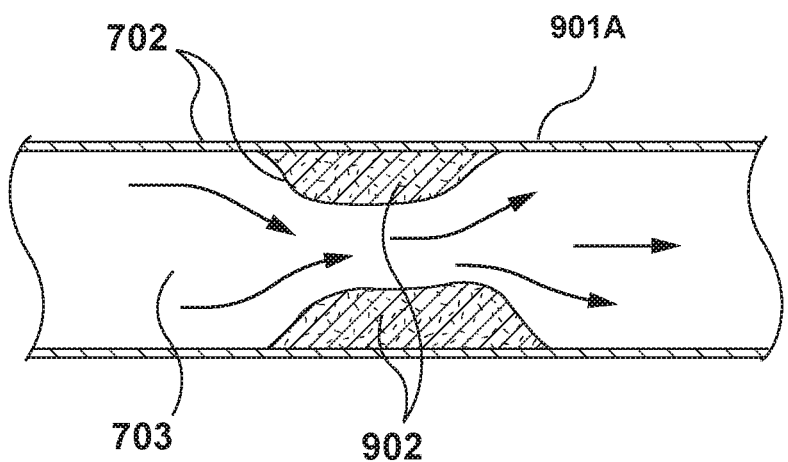
FIGS. 8A-8C illustrate aspects of a computational model modification process.
Figure 8B:
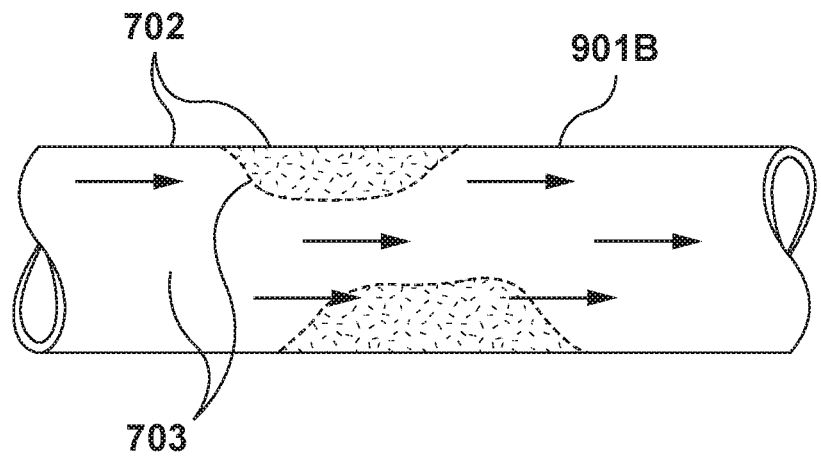
Figure 8C:
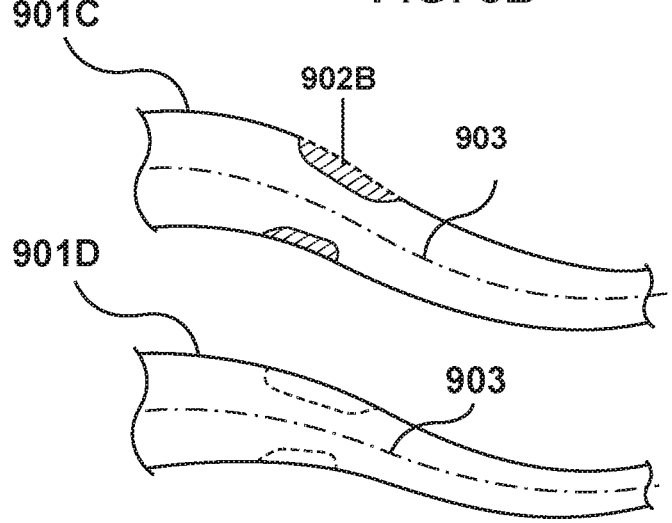

In the computational model 700, removal of a lesion of interest by the modeling module 312 may be performed by using FEA tools to reconstruct the lesion containing vessel without the lesion of interest. FIGS. 8A-8C illustrate aspects of modifying the computational model 700. FIG. 8A illustrates blood flow through a vessel 901A past lesion 902. The walls and lesion of vessel 901A are defined by wall elements 702 and the interior of vessel 901A is defined by interior elements 703. FIG. 8B illustrates blood flow through a modified vessel 901B. The modeling module 312 generates the modified vessel 901B by eliminating the lesion of interest and regenerating the modified vessel 901B as if the lesion of interest did not exist. The modeling module 312 selects points proximal and distal of the lesion of interest and determine a monotonic change in blood vessel diameter between the proximal point and the distal point, so as to model a smoothly changing diameter from the proximal point to the distal point without including the lesion of interest. After blood vessel remodeling, all of the points that were contained within the lesion are identified as interior elements 703 in the updated or modified computational model 700. New wall elements 702 are introduced to the portions of the blood vessel 901B where the newly defined vessel wall is located.

FIG. 8C illustrates an example of removing a lesion of interest where a blood vessel is not straight in the region of the lesion. The vessel 901C includes significant curvature in the region of lesion 902B. In an embodiment, the modeling module 312 identifies the vessel centerline 903 and uses the centerline 903 as an aid in generating a modified vessel 901D. After reconstruction of the modified vessel 901D without the lesion 902B, the modeling module 312 may prompt an operator for confirmation of the change. In embodiments, the modeling module 312 may proceed without requesting confirmation. In embodiments, the operator may perform a manual adjustment of the modified blood vessel 901D. For example, in the case of highly asymmetric lesions, the centerline may be biased to one side or the other which may bias the result.

The modified blood vessel 901B (or 901D) is included in a modified arterial tree (not shown) representing a modified patient vascular model. The modified computational model 700 establishes a modified domain for FEA computations. FEA techniques, as described above, are then repeated by the modeling module 312 to determine a modified velocity and pressure field throughout the modified domain of the modified computational model 700.

Model modification in each of the above cases, for the network model 600 and the computation model 700 results in modified velocity and pressure fields. Modified velocities permit the computation of modified flow rates. In particular, such modification results in increased flow across the region that the lesion of interest was located in prior to model modification due to the loss of flow resistance caused by the presence of the lesion. In embodiments, the local velocity field in the region of the removed lesion of interest may be integrated to determine a modified local flow rate.

Returning again to FIG. 4, in an operation 410 of process 400 a modified FFR value for the lesion of interest is determined by the modeling module 412 according to the modified flow rate in the region of the lesion of interest. As discussed above, removal of the lesion of interest from the vascular model removes resistance to flow, causing a modeled increase in flow rate in the region of the lesion of interest in the modified vascular model. The modeling module 412 is configured to determine the modified FFR values for lesions of interest based on the modified flow rates.

In the network model 600, the modeling module 312 uses the unmodified values of proximal and distal pressures and the flow rate for the vessel branch 601 containing the lesion of interest to determine the resistance to flow provided by the lesion of interest. The resistance to flow of the lesion of interest is then used in conjunction with the modified flow rate by the modeling module 312 to determine a modified pressure drop across the lesion of interest. The modeling module 312 therefore computes a modified pressure drop across the lesion of interest based on the unmodified proximal pressure, the unmodified lesion resistance to flow, and the modified flow rate. In other words, the modeling module 312 determines how much pressure drop across the lesion is required to achieve the same flow rate in the vessel branch 601 as would occur if the lesion were not present. The modified pressure drop is used to determine the modified distal pressure. The modified distal pressure and unmodified proximal pressure are then used in a modified FFR value computation.

In the computational model 700, the modeling module 312 uses the FEA techniques discussed above for computing FFR values employing the modified flow rate. The FEA calculation may be constrained to the region local to the lesion of interest to reduce computing demands. To perform this computation, the FEA analysis is performed according to the unmodified blood vessel structure, e.g., including the lesion of interest, the unmodified inlet pressure, and the modified flow rate.

In an operation 412, process 400 includes identification of lesions for treatment based on modified FFR values. Modified FFR value computation may reveal that lesions of interest having a standard FFR value greater than 0.8, indicating non-treatment, may have a modified FFR value less than 0.8, indicating that treatment may be recommended. The increased flow rate of the modified model results in a greater pressure drop across the lesions of interest which in turn causes the FFR value to be lower than that measured (or calculated) for the patient at baseline. Thus, the modified FFR may identify lesions that should be treated from among a group of lesions determined for no treatment according to standard methods.

Operations 408, 410, and 412 may be repeated for all lesions of interest to identify additional lesions for treatment. The computer system 310 may operate to determine lesions for treatment from among the lesions of interest in an automated fashion and/or with the assistance of an operator. For example, after having identified multiple lesions of interest at operation 408, the computer system 310 may operate to automatically compute modified FFR values for each lesion of interest. In another example, the computer system 310 may receive additional input from the operator via the user interface module 314 to adjust the modified FFR computation. The computer system 310 may prompt the user for approval and verification at any stage of the modified FFR computation as a check on the computational process.

In additional embodiments, the computer system 310 may perform modified FFR computations based on modifications involving a plurality of lesions. The flow fields of the computational model 700 and the network model 600 may be modified according to the removal of more than one lesion. For example, an obstructive proximal lesion may restrict the distal blood flow to a downstream vessel branch including a distal lesion. Because the blood flow rate arriving at the distal lesion is reduced due to the proximal lesion, the standard FFR value of the distal lesion may be skewed. However, the above described method of computing the modified FFR of the distal lesion, based on the removal of a single lesion, may still not yield accurate results, because the flow rate restriction is caused by the proximal lesion. Accordingly, computing a modified FFR value based only on removal of the distal lesion may not provide enough accuracy. Accordingly, the modified FFR value across the distal lesion may be computed according to the removal of both the proximal and the distal lesion. When performing modified FFR computations for a lesion of interest, the modeling module 312 may assess the proximal blood vessel conditions to determine whether one or more additional lesions exist that may modify the blood flow rate that reaches the lesion of interest. Additional lesions may be lesions of interest, clinically significant lesions, and/or any other lesion that affects the flow rate. Additional lesions may be located upstream and/or downstream of the lesion of interest.

According to the above, systems and methods for determining modified FFR values are provided. While only some embodiments according to the present invention have been described herein, it should be understood that they have been presented by way of illustration and example only, and not limitation. Various changes in form and detail can be made therein without departing from the spirit and scope of the invention. Further, each feature of each embodiment discussed herein, and of each reference cited herein, can be used in combination with the features of any other embodiment. For example, and not by way of limitation, any feature of embodiments describing use of the network model 600 may be combined, as appropriate, with any feature of embodiments describing the use of the computational model 700. All patents and publications discussed herein are incorporated by reference herein in their entirety.

What is claimed is:

1. A system for determining modified fractional flow reserve values, comprising:
   an angiographic system configured to receive angiographic images of a coronary vascular system;
   a vascular measurement system configured to receive blood flow measurements of the coronary vascular system; and
   a computer system including at least one processor configured to execute computer instructions to:
      generate a coronary vascular model according to the angiographic images and the blood flow measurements, the coronary vascular model including an arterial tree and a blood flow field describing blood flow and blood pressure,
      identify at least one lesion of interest within the coronary vascular model,
      generate a modified coronary vascular model according to a removal of the lesion of interest, and
      determine a modified fractional flow reserve value for the lesion of interest according to the coronary vascular model and the modified coronary vascular model.

2. The system of claim 1, wherein the at least one processor is further configured to generate the coronary vascular model by generating a network model including a network graph and containing information about a plurality of blood vessel branches, a plurality of vascular nodes, blood pressure within the plurality of blood vessel branches, and blood flow within the plurality of blood vessel branches.

3. The system of claim 1, wherein the at least one processor is further configured to generate the coronary vascular model by generating a computational model according to finite element analysis methods.

4. The system of claim 1, wherein the at least one processor is further configured to generate the modified coronary vascular model by generating a modified flow field including a modified blood flow and a modified blood pressure, and
   wherein determining the modified fractional flow reserve value includes determining the modified fractional flow reserve value according to the modified blood flow.

5. The system of claim 1, wherein the at least one processor is further configured to identify the lesion of interest by requesting input from a user.

6. The system of claim 1, wherein the at least one processor is further configured to identify the lesion of interest according to the angiographic images.

7. The system of claim 1, wherein the at least one processor is further configured to identify the lesion of interest according to the blood flow measurements.

8. The system of claim 1, wherein the vascular measurement system is further configured to receive a fractional flow pressure measurement of the lesion of interest and the at least one processor is further configured to identify the lesion of interest according to the fractional flow pressure measurement.

9. The system of claim 1, wherein the at least one processor is further configured to identify lesions for treatment based on the modified fractional flow reserve value.

10. The system of claim 1, wherein the at least one processor is further configured to generate the modified coronary vascular model according to removal of a plurality of lesions of interest.

11. A computer-implemented method for determining modified fractional flow reserve values, the method to be carried out by at least one processor executing computer instructions, the method comprising:
   receiving, by an angiographic measurement system, angiographic images of a coronary vascular system;
   receiving, by a vascular measurement system, blood flow measurements of the coronary vascular system;
   generating, by the processor, a coronary vascular model according to the angiographic images and the blood flow measurements, the coronary vascular model including an arterial tree and a blood flow field describing blood flow and blood pressure;
   identifying, by the processor, at least one lesion of interest within the coronary vascular model;
   generating, by the processor, a modified coronary vascular model according to a removal of the lesion of interest; and
   determining, by the processor, a modified fractional flow reserve value for the lesion of interest according to the coronary vascular model and the modified coronary vascular model.

12. The method of claim 11, wherein generating the coronary vascular model includes generating a network model including a network graph and containing information about a plurality of blood vessel branches, a plurality of vascular nodes, blood pressure within the plurality of blood vessel branches, and blood flow within the plurality of blood vessel branches.

13. The method of claim 11, wherein generating the coronary vascular model includes generating a computational model according to finite element analysis methods.

14. The method of claim 11, wherein
   generating the modified coronary vascular model includes generating a modified flow field including a modified blood flow and a modified blood pressure, and
   determining the modified fractional flow reserve value includes determining the modified fractional flow reserve value according to the modified blood flow.

15. The method of claim 11, wherein the identifying the lesion of interest includes requesting input from a user.

16. The method of claim 11, wherein identifying the lesion of interest is performed according to the angiographic images.

17. The method of claim 11, wherein identifying the lesion of interest is performed according to the blood flow measurements.

18. The method of claim 11, further comprising:
   receiving a fractional flow pressure measurement of the lesion of interest; and
   identifying the lesion of interest according to the fractional flow pressure measurement.

19. The method of claim 11, further comprising identifying lesions for treatment based on the modified fractional flow reserve value.

20. The method of claim 11, wherein generating the modified coronary vascular model is performed according to removal of a plurality of lesions of interest.

* * * * *